(12) United States Patent
Wagner

(10) Patent No.: US 12,686,007 B2
(45) Date of Patent: Jul. 21, 2026

(54) FLUID SELF-MODULATION

(71) Applicant: 1087 Systems, Inc, Cambridge, MA (US)

(72) Inventor: Matthias Wagner, Cambridge, MA (US)

(73) Assignee: 1087 Systems, Inc

( * ) Notice: Subject to any disclaimer, the term of this patent is extended or adjusted under 35 U.S.C. 154(b) by 664 days.

(21) Appl. No.: 18/029,008

(22) Filed: Mar. 28, 2023

(65) Prior Publication Data

US 2023/0405583 A1    Dec. 21, 2023

Related U.S. Application Data

(63) Continuation of application No. PCT/US2021/052662, filed on Sep. 29, 2021.

(60) Provisional application No. 63/244,337, filed on Sep. 15, 2021, provisional application No. 63/090,681, filed on Oct. 12, 2020, provisional application No. 63/084,799, filed on Sep. 29, 2020, provisional application No. 63/084,651, filed on Sep. 29, 2020.

(51) Int. Cl.
| | |
|---|---|
| *B01L 3/00* | (2006.01) |
| *C12M 1/00* | (2006.01) |
| *C12M 1/26* | (2006.01) |
| *C12M 1/34* | (2006.01) |
| *C12M 1/36* | (2006.01) |
| *C12M 3/06* | (2006.01) |
| *G01N 21/85* | (2006.01) |
| *G01N 21/84* | (2006.01) |

(52) U.S. Cl.
CPC ....... *B01L 3/502715* (2013.01); *C12M 23/16* (2013.01); *C12M 29/10* (2013.01); *C12M 33/07* (2013.01); *C12M 41/30* (2013.01);

*C12M 41/36* (2013.01); *C12M 41/38* (2013.01); *C12M 41/48* (2013.01); *C12M 47/10* (2013.01); *G01N 21/85* (2013.01); *B01L 2300/0654* (2013.01); *B01L 2300/0877* (2013.01); *B01L 2400/0487* (2013.01); *G01N 2021/8411* (2013.01); *G01N 2021/8557* (2013.01); *G01N 2021/8571* (2013.01)

(58) Field of Classification Search
CPC ....... B01L 3/502715; B01L 2300/0654; B01L 2300/0877; B01L 2400/0487; C12M 23/16; C12M 29/10; C12M 33/07; C12M 41/30; C12M 41/36; C12M 41/38; C12M 41/48; C12M 47/10; C12M 47/04; G01N 21/85; G01N 2021/8411; G01N 2021/8557; G01N 2021/8571; C12Q 1/04
USPC ................................................. 422/82.06, 50
See application file for complete search history.

(56) References Cited

PUBLICATIONS

Renfer, Microfluid Nanofluid (2013) 15:231-242. (Year: 2013).*
Rips, Physical Review Fluids 4, 054501 (2019). (Year: 2019).*

* cited by examiner

*Primary Examiner* — Christine T Mui
(74) *Attorney, Agent, or Firm* — NextWave IP Legal Services, LLC; Leon Fortin, Jr.

(57) ABSTRACT

Combining through self-modulation a flow of active media from a working vessel of a bioprocess together with a flow of reference media and making a time- and/or spatially-resolved referenced optical measurement of the active vs reference media in a confined flow region and time, such that the two liquids are measured in substantially identical conditions.

16 Claims, 12 Drawing Sheets

FIG. 8
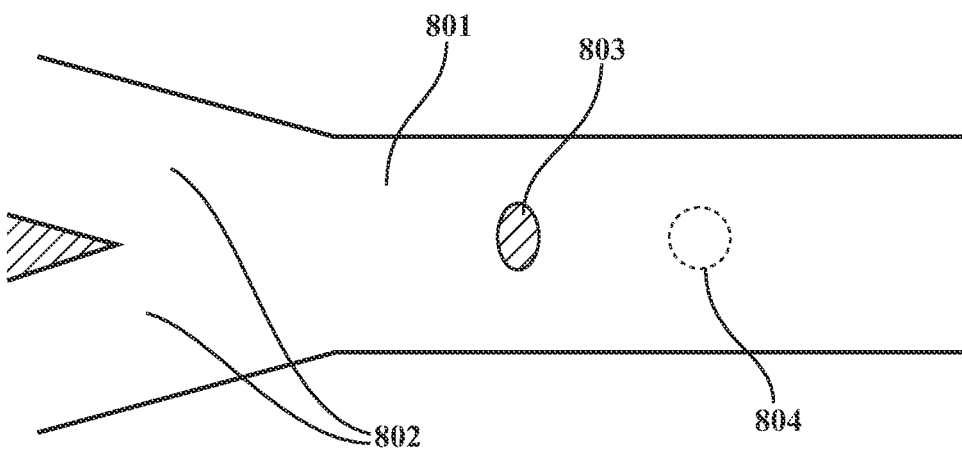
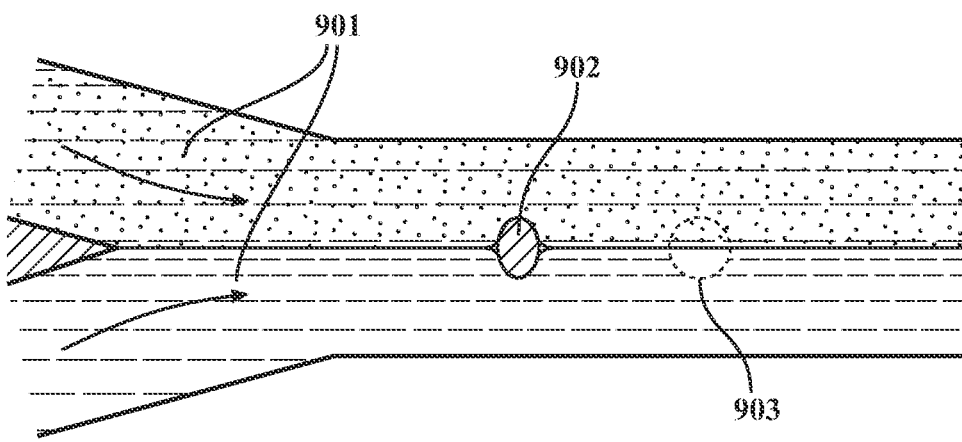
FIG. 9

FIG. 12
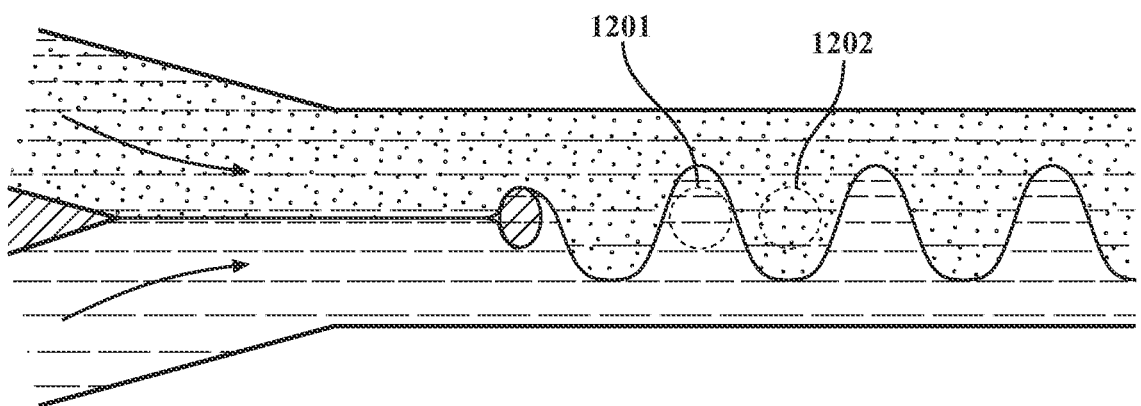
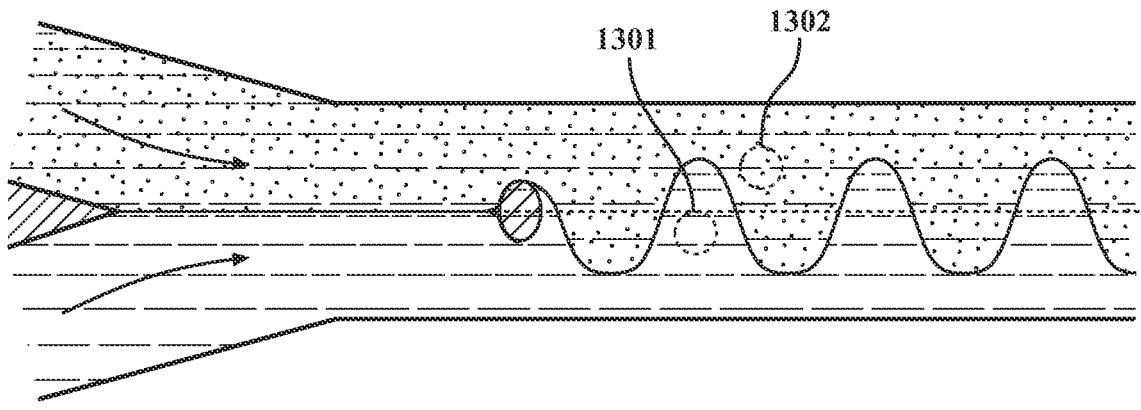
FIG. 13

1901

1902

FLUID SELF-MODULATION

CLAIM TO PRIORITY

This application is a National Phase filing of PCT Application Serial No. PCT-US2021-052662, the entirety of which is incorporated herein by reference. PCT Application Serial No. PCT-US2021-052662 claims the benefit of the following provisional applications, each of which is hereby incorporated by reference in its entirety: U.S. Provisional Patent Application Ser. No. 63/084,651, filed Sep. 29, 2020; U.S. Provisional Patent Application Ser. No. 63/084,799, filed Sep. 29, 2020; U.S. Provisional Patent Application Ser. No. 63/090,681 filed Oct. 12, 2020; and U.S. Provisional Patent Application Ser. No. 63/244,337 filed Sep. 15, 2021.

BACKGROUND

Field

The methods and systems described herein pertain to measurement and analysis of biochemical constituents through non-contact means including use of self-modulation, optical sensing, and the like.

Description of the Related Art

Generally in the field of bioprocessing, bioprocess efficiency and stability can be highly sensitive to media conditions. Additionally, in bioprocessing where cells are producing a target product, it is desirable to harvest that product at a concentration that may be product-specific. A number of basic media conditions such as pH and dissolved $O_2$ concentration generally characterize noninvasive measurement techniques. For more sophisticated media constituent measurements, however, techniques are still evolving.

One range of techniques of interest include optical measurements of the cell media, for example, the application of spectroscopic analytical techniques. Included in these are UV/VIS spectroscopy measuring electronic transitions, as well as vibrational (e.g., absorption and Raman) spectroscopy. These techniques may be performed online or inline in a closed system, and potentially provide rich information on the biochemical state of the media and/or cells by measuring constituents including cells, proteins, metabolic products, metabolite concentration, nutrients, waste products, and the like.

A general issue with existing spectroscopic techniques, however, is an undesirable trade-off between specificity and sensitivity in attempting to achieve reliable measurements on specific media and/or cell constituents. Vibrational spectral signals in particular are often weak (especially at low concentration), and as a result suffer from significant background variations that may be due to variations in media conditions (media temperature, batch-to-batch media variations, etc.), environmental factors (temperature-, humidity- or time-dependent variations in optical transmission/reflections of components), or optical component performance (temperature- or time-dependent variation in output of light sources, or detector signal, baseline or noise levels).

Examples of the challenges in optical bioprocess monitoring may be found in: (i) *Probeless non-invasive near-infrared spectroscopic bioprocess monitoring using microspectrometer technology*, Zimmerleiter et al, Analytical and Bioanalytical Chemistry (2020) 412:2103-2109: discussion of NIR microspectroscopy potential for non-invasive bioprocess monitoring, but also highlights the challenges of moving baselines and establishing reference levels in these measurements; and (ii) *A method based on light scattering to estimate the concentration of virus particles without the need for virus particle standards*, Makra et al, MethodsX, Volume 2, 2015, Pages 91-99, which discussed the problems of background signals in bioprocess measurements, each of which is incorporated herein in its entirety by reference.

Many efforts to do precise spectral measurements of bioprocess media have been undertaken, at multiple wavelength ranges. For example, a basic measurement of cell density is often performed using an opacity (extinction) measurement at 600 nm, where light scattering by cells in the optical path reduces the amount of light reaching the detector.

However, it would be highly desirable to measure not just biomass, but biochemical constituents through non-contact means in a way that is compatible with on-line or in-line, real-time measurements. Example state of the art techniques include: (i) US Pat. Pub. No. 2015-0247794 A1, Apparatus and Method for Automated Process Monitoring and Control with Near Infrared Spectroscopy, Olesburg et al. describes a bioprocess monitoring system based on near infrared (NIR) spectral measurements, with sophisticated referencing within the optical apparatus, but no way to achieve referencing of the active media being measured against reference media, except by off-line measurements; and (ii) *Applications of Raman Spectroscopy in Biopharmaceutical Manufacturing: A Short Review*, Buckley et al, Applied Spectroscopy, 2017, Vol. 71(6) 1085-1116, provides extensive detail on efforts to use Raman vibrational spectroscopy to characterize bioprocesses. There is extensive discussion of the effects of having large baseline signals in the cell media (and due to fluorescence), and the resulting difficulty of extracting small signals of interest that are associated with changes in the active media in the bioprocess, each of which is incorporated herein in its entirety by reference.

Further, use of long-wavelength infrared vibrational spectroscopy to characterize analytes in bioreactors is described in: *Multi-analyte quantification in bioprocesses by Fourier-transform-infrared spectroscopy by partial least squares regression and multivariate curve resolution*, Koch et al, Analytica Chimica Acta 807 (2014) 103-110, which highlights the small changes in IR spectra associated with target compounds vs background media components. In the paper, the authors reference media spectra against water and fresh media standards, but do so manually on a prism, solely for the purpose of calibrating the system, which is incorporated herein in its entirety by reference.

In bioprocessing scenarios it is desirable to measure solid constituents of the bioreactor broth; such constituents may include but are not limited to microcarriers or microcarrier debris, cell aggregates, cells, cell debris, extracellular vesicles, viruses, protein aggregates, proteins, or other media components that are the product or byproduct of the bioreaction. Use of optical means to measure these constituents is challenged by the many constituents of the active media/broth that may cause a dramatically variable baseline—where the variations in baseline optical conditions far outweigh the signal from the particles of interest. In other cases other larger particles may cause optical obstructions/scattering that cause noise in the output signal.

In summary, challenges for bioprocessing include: bioprocesses are very sensitive to media conditions; media conditions can also be a powerful indicator of biological activity; opening of system for media extraction runs risk of contamination, therefore a closed system with non-contact monitoring is highly desirable; low signal and signal-to-noise is an issue in current methods; background variations from light sources, detectors, mechanical, temperature, and the like accentuate these challenges; further constituents of an active media/bioreactor broth cause a dramatically variable baseline.

There remains a need for bioprocessing constituent measurement methods and systems that overcome these many challenges.

In the art field of liquid optical path modulation spectroscopic analysis of liquids and specifically analyses within liquids can take advantage of the availability of new light sources such as quantum cascade lasers (QCLs) that provide sufficient optical power to penetrate liquids in microfluidic channels at appropriate wavelengths for analysis of chemical and biochemical compounds.

A number of designs for instruments in this category have been proposed. It was recognized by the present inventor that a design where the optical path is modulated between at least one liquid to be analyzed or analyte-bearing liquid ("analyte liquid") and a reference liquid that is substantially identical to the analyte liquid, and is measured under substantially identical conditions (temperature, pressure, flow rate, etc.) could greatly enhance the sensitivity of a measurement to small changes in the target analyte(s), as described in: (i) U.S. Pat. No. 8,941,062: SYSTEM FOR IDENTIFYING AND SORTING LIVING CELLS, M. Wagner at al.; (ii) U.S. Pat. No. 8,502,148: SINGLE PARTICLE QCL-BASED MID IR SPECTROSCOPY SYSTEM WITH ANALYSIS OF SCATTERING, M. Wagner at al.; and (iii) U.S. Pat. No. 9,835,552: CYTOMETRY SYSTEM WITH INTERFEROMETRIC MEASUREMENT, M. Wagner et al., each of which is incorporated herein in its entirety by reference.

Further, several iterations upon this idea to achieve liquid-optical path modulation using combinations of liquid switching and optical switching have been proposed, including: (i) U.S. Pat. No. 9,377,400: Motion modulation fluidic analyzer system, M. Wagner et al.; (ii) U.S. Pat. No. 10,180,388: Scanning Infrared Measurement System, M. Wagner et al.; (iii) U.S. Ser. No. 15/605,962: Microfluidic Methods and Apparatus for Analysis of Analyte Bearing Fluids, C. Marshall et al.; and (iv) U.S. Ser. No. 16/257,112: FLUID ANALYZER WITH MODULATION FOR LIQUIDS AND GASES, C. Marshall et al., each of which is incorporated herein in its entirety by reference.

A drawback of these valve-modulated systems is the requirement for reliable, continuous modulation of liquid flows by mechanical means. This system of valves and switches significantly increase the complexity of the instrument, increase its size, and potentially reduce its reliability. Particularly in systems that may be used for online process, product, or equipment monitoring, it would be desirable to reduce or eliminate the use of these electromechanical components. A further disadvantage is the relatively slow maximum frequency of modulation. For example, a commercial system available from RedShift Bioanalytics (Burlington, MA, USA), which already performs very well compared to conventional FTIR instrumentation, uses a modulation frequency of only 1 Hz (*Shaping IR Spectroscopy into a Powerful Tool for Biopharma Characterizations*, Batabyal et al, BioPharm International, May 2020 is hereby incorporated by reference in its entirety). Slow modulation has a number of effects: it requires generating and measuring optical and electrical signals in a regime where noise is generally higher (due to 1/f noise and environmental noise sources such as electrical interference and mechanical vibrations), and it requires more time to capture a signal—which is compounded if a tunable optical source is used to interrogate the liquid and multiple wavelengths must be measured. This in turn opens the possibility of further drifts and noise, as well as the requirement for more analyte to flow through the analyzer.

SUMMARY

The methods and systems of graded bioprocess constituent measurement may use a combined flow of active media from a working vessel of a bioprocess together with a flow of fresh cell media, making a time- and/or spatially-resolved referenced optical measurement of the active vs fresh media in a confined flow region and time, such that the two liquids are measured in substantially identical conditions. These methods and systems of graded bioprocess constituent measurement enables highly-sensitive measurements of the differentials between active and fresh media constituents such a cell nutrients, cells, cell waste products, contaminants, and/or desired bioprocess products such as proteins, exosomes, viral particles, RNA/DNA, or cells laden with the desired product.

Compared to existing optical bioprocess measurements, where active media is measured by itself, whether through the use of a probe in the bioreactor, or through measurement of media that is removed from the bioreactor (in line, or sampled), the methods and systems of graded bioprocess constituent measurement dramatically reduces background effects from the media itself (because the major constituents are already present in the fresh media, against which the active media is measured), and from the measurement apparatus (where time, temperature, humidity and other factors may alter the properties of both active and passive components in the optical train). Moreover, as the methods and systems of graded bioprocess constituent measurement may enable measurement of both liquids (alternating or simultaneous) at high frequencies (>1 Hz), it may allow significant reduction in "1/f" noise that plagues static measurements such as those typically performed in optical bioprocess measurements.

The methods and systems of graded bioprocess constituent measurement contemplate measurements where active media is extracted from a bulk-fed bioreactor (where fresh media is added only at the start of the reaction) is measured by way of this technique against a fresh sample of the media (typically the same batch used to feed the reaction) held at substantially identical environmental conditions.

However the methods and systems of graded bioprocess constituent measurement may be applied to continuous or "perfusion" bioprocesses where fresh media is continuously added to a bioreactor in order to sustain the desired reaction, and simultaneously active media is extracted to maintain volume, to eliminate waste, and/or to harvest reaction products. In this configuration the methods and systems of graded bioprocess constituent measurement use the fresh media flow and extracted active media flow to make in-line, real-time measurements of the change in constituent composition and/or state of the active media vs fresh media.

Again, a highly desirable manner in which to measure these components would be through optical means, as these can allow in-line or on-line, real-time measurements within a closed system.

Further, these methods and systems may use a number of fluidic flow architectures and optical interrogation techniques previously disclosed by the inventor, including but not limited to those described in the following: (i) U.S. Ser.

No. 16/282,903. Use of vibrational spectroscopy for DNA content inspection, Wagner et al.; (ii) U.S. Pat. No. 10,261,012. Cytometry system with interferometric measurement, Wagner et al.; (iii) U.S. Ser. No. 10,677,710. Scanning infrared measurement system, Wagner et al.; (iv) U.S. 62/705,709. Self-modulating liquid analyzer, Wagner; and (v) U.S. 63/032,667. Fluid analyzer system with self-modulation, Wagner, all of which are incorporated herein in their entirety by reference.

Self-Modulation

In embodiments, a system for measuring fluids and components within fluids may include a flow channel configuration where at least two fluids flowing at a range of velocities cause vortex shedding in a pattern that allows modulated optical measurements to be performed, thereby increasing the sensitivity of these optical measurements, while providing a signal that is proportional to the relative properties of the two fluids.

The methods and systems of microfluidic self-modulation may include a range of mechanical configurations designed to provide self-modulation at lower Reynolds numbers, i.e. with lower flow rates. This can be advantageous where the amount of sample is limited, or potentially where pressure is limited. An exemplary embodiment of a fluid mixing flow chamber based on a flexible membrane placed in a channel is given in: *Enhanced Mixing at Inertial Microscales using Flow-Induced Flutter*, Aaron Rips and Rajat Mittal, Physical Review Fluids, 4(5), p. 054501 (doi.org/10.1103/PhysRevFluids.4.054501), which is hereby incorporated in its entirety by reference. Note that the authors of this paper targeted fluid mixing at relatively low Reynolds numbers with the design. In the present disclosure, while it may be desirable to transition into the mixing regime for certain measurements described herein, for modulated measurements, it is desirable to be in a transition flow regime, where vortices are shed from an obstacle in a predictable manner without extensive mixing through a measurement section of the channel. In designs where a fixed obstruction such as a cylinder or rectangular cylinder are used this regime occurs roughly with Reynolds numbers of 100-200.

With the use of a flexible membrane that can itself deform within the flow, it is possible to achieve modulated flow at inertial scale Reynolds numbers (0-100). In an example a Reynolds number as low as 15 is described in the paper by Rips et al. A flexible membrane embodiment may be used in the laminar flow mode at very low flow rates (for example <10), in the transition (vortex shedding) mode at medium-low (for example 10-100) for modulated measurements, and medium-high to high (for example >100) for mixing measurements. Descriptions of liquid flows in these regimes, together with appropriate Reynolds numbers to achieve them may be found in: *On the onset of vortex shedding from 2D confined rectangular cylinders having different aspect ratios: application to mixing fluids*, Ortega-Casanova, Chemical Engineering and Processing—Process Intensification (2017); and *Vortex shedding from confined micropin arrays*, Renfer et al, Springer Microfluid Nanofluid (2013), which are hereby incorporated by reference, in their entirety. In addition, an implementation of vortex flows in microfluidics (for a different application) is described in: *Intracellular delivery of mRNA to human primary T cells with microfluidic vortex shedding*, Jarrell et al, Nature Scientific Reports (2019), which is hereby incorporated by reference, in its entirety.

Techniques for microfluidic self-modulation described herein may be used to measure the relative properties of two or more fluids, as exemplarily described herein, and/or to measure changes as a result of interactions between the fluids, for example chemical reactions that result in changes in optical features of interest, such as index, fluorescence, absorption, scattering, polarization, and other changes that are measurable using optical sensors that observe sections of the flow channel downstream from the obstruction.

In embodiments, the fluid modulation inherent in the embodiments described herein can be tuned based on the flow rate, channel diameter, and obstruction geometry, at least as described in the incorporated references. One significant advantage is that the self-modulation can occur at relatively high frequencies, for example ≥10 Hz, or ≥100 Hz, or ≥1000 Hz where the resulting optical signals may be measured and processed with high signal-to-noise ratios, being isolated from typical 1/f noise sources and environmental noise sources. Further, one may use AC-coupled or AC-sensitive detectors that provide superior performance to DC detectors, particularly in the MWIR, LWIR, and THz ranges.

Pyroelectric detectors are uncooled (and therefore lower complexity and cost), but are AC-coupled. These detectors may be arranged in differential pairs; for example, if two optical paths through the detection region are used, then the difference in extinction between the two liquids can be measured at the frequency of the vortices produced.

For photoconductive or photovoltaic detectors, a modulated signal is also preferable, and often optimal signal-to-noise (SNR) ratio is achieved at ≥10 Hz, ≥100 Hz, or ≥1000 Hz depending on the detector and circuit characteristics. Compared to valve-actuated systems for modulating fluid flow, the methods and system of microfluidic self-modulation described herein enable differential measurements between fluids with much lower complexity, and potentially far higher frequencies. For example, Polycrystalline lead sulfide detectors (PbS) or Polycrystalline lead selenide detectors (PbSe) for the MWIR spectral range often achieve their best signal-to-noise ratio (SNR) at ≥100 Hz or even ≥1000 Hz frequency, due to higher noise at low frequencies. Likewise Indium antimonide (InSb) and mercury cadmium telluride (MCT) photoconductive detectors suffer from additional 1/f noise at <100 Hz, making operation at >100 Hz desirable.

The methods and systems described herein make possible self-modulating flows in the ≥10 Hz, ≥100 Hz, ≥1000 Hz ranges depending on pressure, channel dimensions, and obstruction design (including but not limited to circular column, rectangular column, and flexible membrane designs disclosed herein), thereby significantly enhancing the SNR achievable in optical measurements of the fluids within the flow.

The methods and systems of microfluidic self-modulation may be useful with a number of optical detection techniques for chemical, biochemical, particle, and biological measurements of analyte fluids, including:

a. Ultraviolet (UV) absorption spectroscopy. For example, the methods and systems of microfluidic self-modulation may be applied with a UV transmission configuration to detect small amounts of DNA or RNA in a solution; moreover polarization may be used in this configuration to measure circular diochroism to gather structural information; two solutions may be run side-by-side after treatment of one of them to elucidate changes with high sensitivity.

b. UV or VIS fluorescent measurements. For example, the methods and systems of microfluidic self-modulation may be applied using a UV excitation source to measure a solution with fluorophore-tagged biochemicals.

For example the analyzer may be used to detect trace concentrations of proteins or antibodies that have been fluorescently tagged. The system may be used in the absence of labels using the inherent autofluoresence of some target analyses.

c. Visible-light (VIS) spectroscopy. The methods and systems of microfluidic self-modulation may be used with visible light source and detectors or cameras. In one embodiment, the analyzer may be used to measure scattering by nanometer-sized particles in the fluid, such as aggregates of proteins, extracellular vesicles, or nanometric pollutants captured from a gas stream.

d. Near infrared (NIR) spectroscopy. The methods and systems of microfluidic self-modulation may be used with spectrometry in the NIR range to measure liquid composition against a reference. For example, it may be used to check oils against a reference to establish authenticity. In another example, it may be used with oils in machinery or electrical applications to check for degradation against a new sample. In another application, the methods and systems of microfluidic self-modulation may be used to monitor biological processes, such as those occurring in a bioreactor, by measuring fresh vs extracted cell media, and thereby enabling the periodic or real-time monitoring of nutrient consumption and cell metabolism products.

e. Raman spectroscopy. The methods and systems of microfluidic self-modulation may be used with Raman spectroscopic systems for monitoring liquids with high spectral detail. The modulation aspect of the methods and systems of microfluidic self-modulation (including higher-speed modulation than can be achieved by valve-based liquid switching) can provide a significant advantage in Raman to improve signal-to-noise characteristics.

f. THz spectroscopy.

g. Scattering measurements made in these optical ranges, either independently or together with absorption.

h. And polarization-dependent measurements made in these optical ranges.

In embodiments, the methods and systems of microfluidic self-modulation disclosed herein may enable very compact and low cost liquid measurement systems that nonetheless provide high sensitivity measurements.

These and other systems, methods, objects, features, and advantages of the present disclosure will be apparent to those skilled in the art from the following detailed description of the preferred embodiment and the drawings.

All documents mentioned herein are hereby incorporated in their entirety by reference. References to items in the singular should be understood to include items in the plural, and vice versa, unless explicitly stated otherwise or clear from the text. Grammatical conjunctions are intended to express any and all disjunctive and conjunctive combinations of conjoined clauses, sentences, words, and the like, unless otherwise stated or clear from the context.

BRIEF DESCRIPTION OF THE FIGURES

The disclosure and the following detailed description of certain embodiments thereof may be understood by reference to the following figures:

FIG. 8 depicts a microfluidic channel structure embodiment of an aspect of the methods and systems of self-modulation disclosed herein.

FIG. 9 depicts an exemplary low-velocity, low-Reynolds number embodiment of the present disclosure.

FIG. 12 depicts an embodiment with a plurality of optical interrogation regions.

FIG. 13 depicts an alternate plurality of optical interrogation regions embodiment.

DETAILED DESCRIPTION

Figure 1:
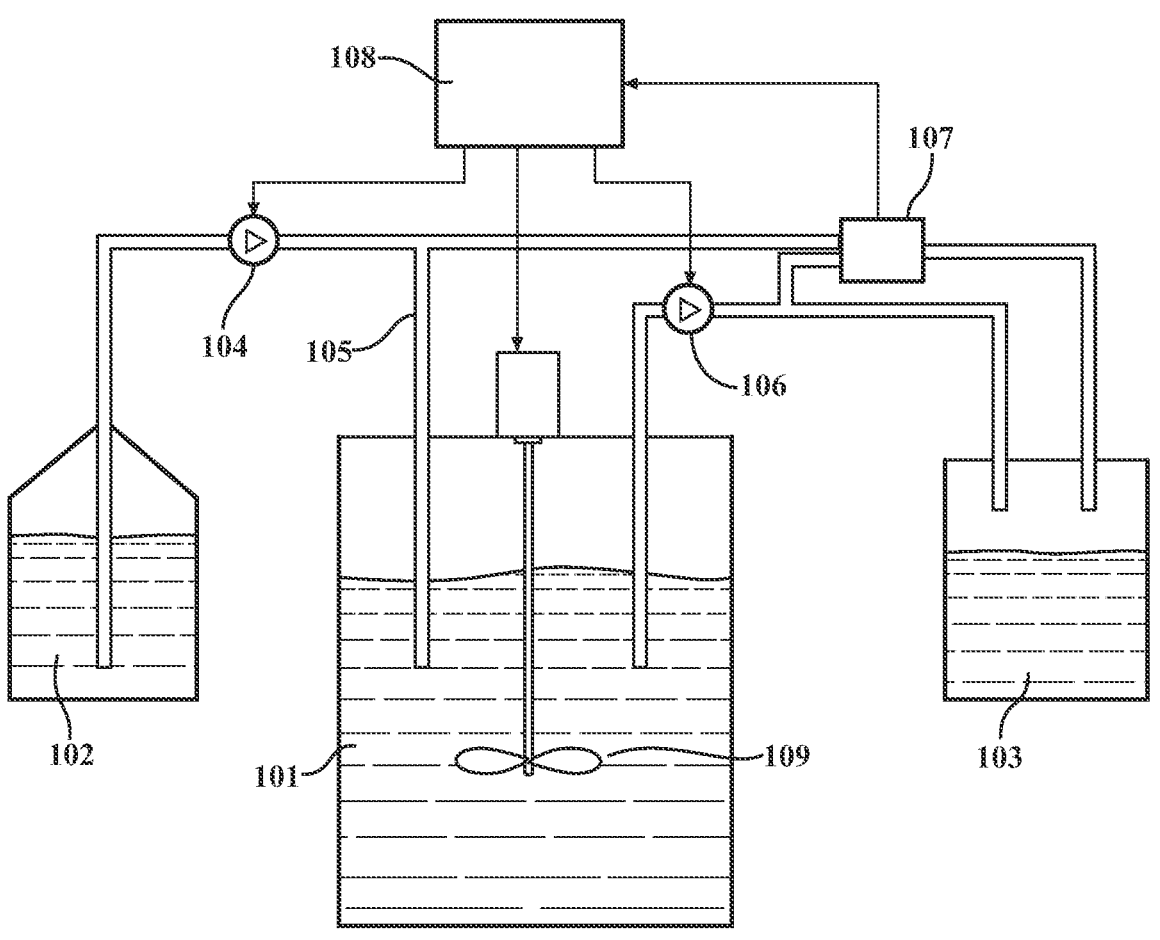
FIG. 1 depicts a perfusion bioprocessing system embodiment of the methods and systems of graded bioprocess constituent measurement disclosed herein.

In embodiments, the methods and systems of graded bioprocess constituent measurement may include self-referenced optical monitoring using fresh media and active media in parallel to provide high-sensitivity measurements while removing background variations. Typical wavelengths may include: UV, VIS, NIR, MWIR, LWIR, THz, and others. Modalities may include: Absorption, scattering, polarization, VCD, Raman scattering, optical phase delay based on refractive index, and the like. Light sources may include: LEDs (+filters), pulsed or other lasers, QCL, and the like. In embodiments, these methods and systems may support various liquid configurations including, without limitation: parallel flow/interface scatter; alternating flow; parallel flow/scanning; parallel flow with moving front; full example: self-modulating parallel flow, and the like. In embodiments, system configurations may include fresh media feed all through detection; partially through detection; flow control in self-modulating; control of fresh media feed; and the like.

One advantage of many of the methods and systems of graded bioprocess constituent measurement is the application of in-line detection of cells, cell clusters, aggregates that avoids filtering and/or diverting a measured media.

In an aspect, one or more filtration steps may be applied to an active bioprocess media in order to isolate and produce two differently-filtered streams. One stream is filtered to effectively represent baseline conditions in which a target media constituent/component resides (e.g., the target component is filtered out); the other includes the target constituent/component. The two streams are then flowed, such as with a fluid combiner, into a common flow chamber that optionally includes an optical interrogation region, where they are optically interrogated in a manner that accentuates the signal from the target constituent, against the common background represented by the more-filtered media stream.

In embodiments, the methods and systems of graded bioprocess constituent measurement may be applied to measure and analyze solid matter in bioprocesses, either in a closed loop or as "broth" is extracted, and potentially after one or more levels of filtration. Besides multi-stage conventional filtration as described above, a number of microfluidic configurations for separating, distributing or isolating particles by size and shape may be incorporated into the methods and systems of graded bioprocess constituent measurement disclosed herein. In an aspect, two or more streams or sections of flow resulting from these architectures may be utilized in order to make relative measurements for providing very high sensitivity analysis of a component that appears in differential quantities/forms in the two or more streams, while allowing background variations to be effectively removed from the measurement. Examples of separation architectures that may be used herein are described in: (i) *A Review on Deterministic Lateral Displacement for Particle Separation and Detection*, Salafi et al, Nano-Micro Letters (2019) provides description of dynamic lateral displacement (DLD) architectures to separate or sort and particles within a liquid using arrayed structures, in a manner that may be integrated into embodiments of the present disclosure; (ii) *Progress of Inertial Microfluidics in Principle and Application*, Guo et al, Sensors 2018, 18, 1762; doi:10.3390/s18061762, describes a range of microfluidic designs that may direct solid (or droplet/immiscible liquid) components in a liquid into a particular portion of a microfluidic flow as part of embodiments of the present disclosure; and (iii) *A review of sorting, separation and isolation of cells and microbeads for biomedical applications: microfluidic approaches*, Dalili et al, Analyst (2019) describes a wide range of particle separation architectures implemented in microfluidics, that may be combined with the other elements disclosed herein to measure specific elements of a liquid containing a range of components, all of which are incorporated herein by reference, in their entirety. Use of one or more of these techniques for separating/isolating contents of a fluid stream by size, shape and/or mechanical properties by the methods and systems of graded bioprocess constituent measurement described herein, can subsequently measure the resulting streams (whether discrete or continuous in terms of their contents' properties) against one another in a simultaneous or relatively high-frequency multiplexing measurement in order to isolate the differential optical properties of the streams, which in turn may be used to characterize the contents of the overall fluid stream.

FIG. 1 shows a perfusion bioprocessing system incorporating the methods and systems of graded bioprocess constituent measurement disclosed herein. A bioreactor 101 contains cells in a growth medium. The bioprocessing system is supplied with fresh cell media 102 using a feed pump 104 through feed 105 as controlled by a bioreactor management/control system 108. A fluid handling system may include a bleed pump 106 to remove bioreactor media into a bleed container 103 (which may also be used to collect the desired products from the bioreaction). A sensing system embodiment for graded bioprocess constituent measurement as disclosed herein, shown as 107, draws simultaneously from the fresh media stream supplied by pump 104 and the active/used media stream supplied through pump 106. Additional filtration may be placed ahead of the sensing system 107 in order to reject solids (or solids above a certain diameter) directly into the bleed container. The sensing system 107 (a) ensures both fresh and active media streams are at approximately the same temperature; (b) combines the fresh and active media streams into a flow that flows through a common fluidic channel with an optical interrogation region, where they can be measured optically under substantially identical conditions, such as with an optical characteristics measurement subsystem; (c) illuminates these flows with a radiation source; (d) measures the transmitted, scattered, or diffracted light as the light passes through the two streams; (e) calculates (optionally with an electronic processing system) at least a differential in one or more physical and/or biochemical characteristics of the fresh and active media based on the differential in optical characteristics [note: absolute levels may also be measured/calculated in this system, as would occur in a conventional optical bioprocessing measurement]; and (f) supplies these measurements to the bioprocessing system controller 108, which may adjust operating conditions accordingly, such as: feed new fresh media and withdraw/remove used media; feed fresh cells and/or extract cell mass; remove bioprocessing products; increase or slow the mixing rate using a mixing system 109; adjust gas pressure and/or relative gas concentrations; or adjust other operating conditions according to biochemical constituent levels measured by the sensing system 107. In embodiments, a bioreactor may use cells to produce viruses, including one or more of viruses for vaccines, viruses for gene therapy that may include lentiviruses, Adendo-Associated viruses and the like.

Figure 2:
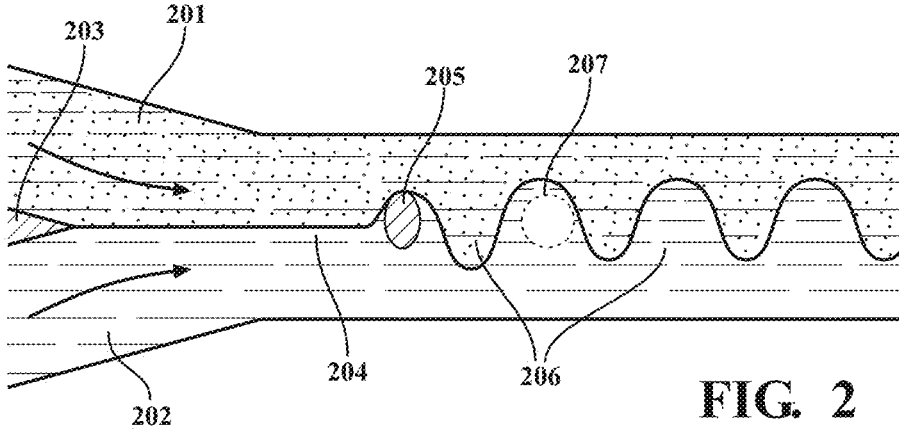
FIG. 2 depicts a sensor portion embodiment of an exemplary system.

FIG. 2 depicts one schematic embodiment of the sensor portion of the methods and systems of graded bioprocess constituent measurement disclosed herein. Two flows, a fresh media flow 201 and an active media flow 202 are merged via a fluidic junction 203 into a laminar flow 204 with a distinct boundary between the two flows. In this example a self-oscillating flow field is set up using an obstruction 205 that causes vortices 206 to be shed downstream at certain flow conditions. Within this downstream section there is an optical interrogation region 207. Light is passed through the interrogation region, where it at successive timepoints interacts with substantially the fresh media, substantially the active media, and also the interfaces between the active and fresh media. Within this design a number of optical measurements may be made. For example, optical extinction measurements may be made at one or more wavelengths, where the light produced by one or more light sources passes through the optical interrogation region, and only that light which passes directly through (vs scattered) strikes one or more detectors on the far side. In this case, a broadband light source may be used, and an array of detectors used on the receiving end, with the appropriate filters or grating to separate the wavelengths and direct them to the appropriate detectors. In another embodiment, a tunable laser source may be used, and the light passing through the optical interrogation region is directed to a single detector. In another embodiment, light that is passed directly through the optical interrogation region without scatter or diffraction is blocked, and only scattered light is captured and directed towards a detector; this may be done at one or more wavelengths; such a configuration may be used to detect particles or aggregates (e.g., aggregates of molecules) within the active media with high sensitivity; for example to measure the level of viral particles, exosomes, microcarriers (with or without attached cells), cell debris, or protein aggregates that result from the bioprocess.

Figure 3:
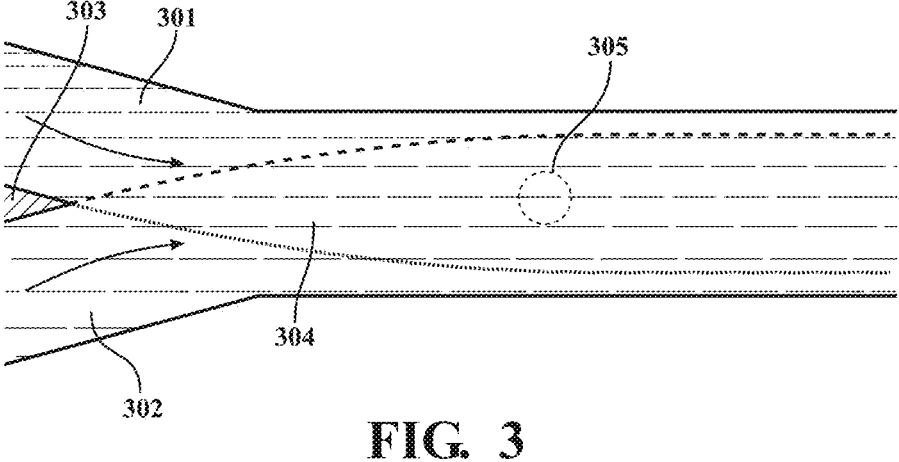
FIG. 3 depicts a liquid handling embodiment of the present disclosure.

FIG. 3 depicts another embodiment of the liquid handling portion of the present methods and systems of graded bioprocess constituent measurement disclosed herein, where the fresh media 301 and active media 302 flows are combined at a junction 303 into laminar flow in a common flow path 304 where an optical interrogation region 305 is located. Pressure of one or both of the fluids is regulated so as to move the laminar junction between the fluids laterally relative to the flow, and such that the optical interrogation region alternately samples the fresh media, the active media, and the interface between the mediums. In this manner a time-resolved measurement of the differentials in optical characteristics of the fresh and active media may be measured with high precision, and largely eliminating common baseline and drift factors.

Figure 4:
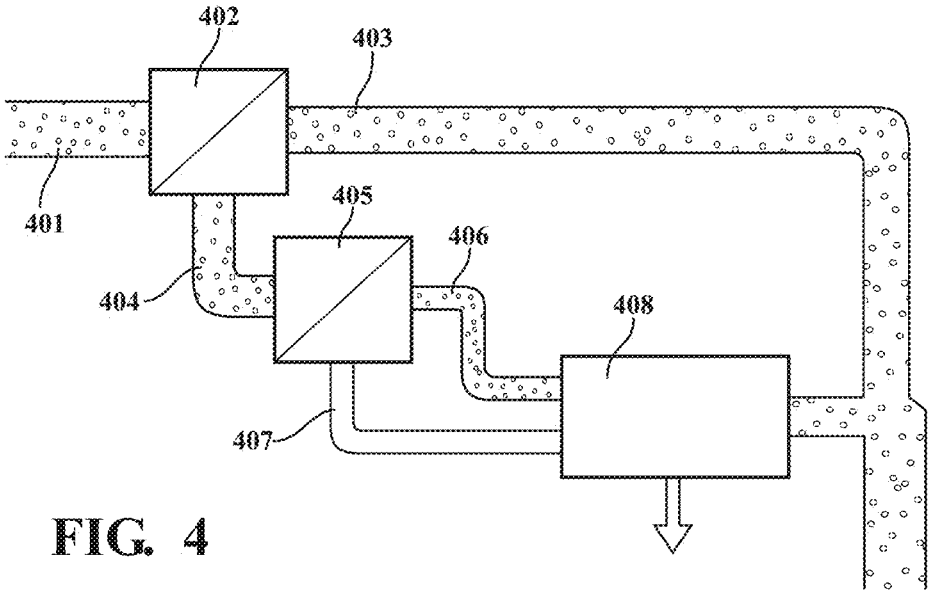
FIG. 4 depicts a multi-stage filtration embodiment of the present disclosure.

FIG. 4 shows an example embodiment of the present methods and systems of graded bioprocess constituent measurement disclosed herein. In this example, the liquid pulled from the bioreactor 401 contains both cell aggregates and single cells within the media; a first filtration stage 402 is used to separate the aggregates in order to produce a rejected stream 403, which may be routed to a harvesting or waste vessel, or cycled back into the bioreactor; and a stream 404 which does not contain aggregates. A second filtration stage 405 is then used to separate the cell-laden stream 406 from a stream that has no cells 407. These two streams are then used as the "signal" and "reference" levels in the opto-fluidic sensing subsystem 408, which through the use of a common flow channel and parallel (spatial and/or temporal) optical interrogation, isolates the signal due to the cells. In this embodiment, the measurement may be made on a single cell at a time, or multiple cells for aggregate measurements. There may be one optical sensing system/subsystem to characterize the cell density (for example, a visible scattering measurement, or optical density measurement), and a separate optical system for measuring more detailed cell optical characteristics, for example absorption and/or scattering at multiple wavelengths in order to deduce biochemical contents. Such contents could include lipids, nucleic acids, proteins, polymer chains, organelles, etc.

It should be understood that various embodiments similar to those depicted in FIG. 2 are possible to isolate and measure a wide variety of bioreactor constituents, with one or more filtration stages to create the measured streams, and potentially with multiple streams measured.

Figure 5:
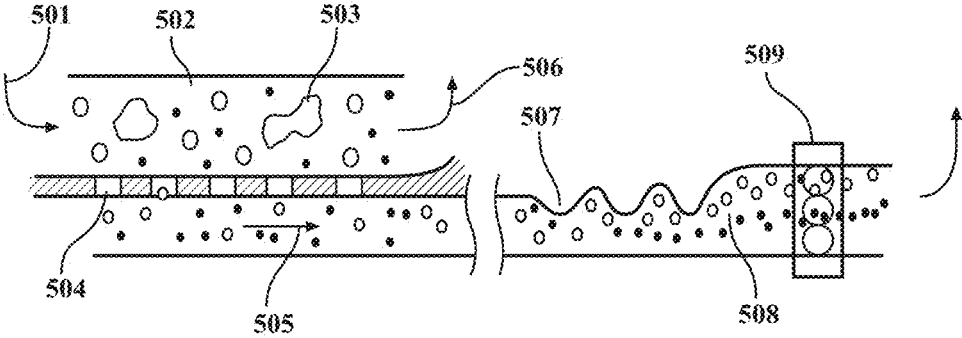
FIG. 5 depicts a flow filtration embodiment of the present disclosure.

FIG. 5 shows a schematic of a portion of an embodiment of the present methods and systems of graded bioprocess constituent measurement disclosed herein. In this example, a liquid flow 501 from a bioreactor process with multiple types of solid or immiscible liquid components runs through a first filtration stage 502 (shown here as a tangential flow filtration system, with filter membrane 504) where large solids 503 are excluded and returned with the stream 506, while smaller particles are allowed into a stream for analysis 505. The stream for analysis then enters a size-separation section represented here by 507, which should be understood to be one of multiple configurations described above, where the effect of this section is to distribute particles (including but not limited to cells, cell aggregates, cell fragments, protein aggregates, exosomes, and immiscible droplets) by size and/or shape substantially perpendicular to the flow direction, such that in a downstream section 508 there are sections of the flow that are rich in different components. In some cases there may be substantially a single type of component that is spatially separated from the carrying fluid on its own. In others there will be multiple discrete flows of different particle types; in others, a gradient of particles by size. Importantly, these flows remain separate such that they pass through an optical interrogation region 509. In the optical interrogation region, the flow and optical measurements are configured such that relative measurements of the different sub-flows are made, in order to remove the common properties of the liquid and component analytes, and extract only the difference that results from the gradation of particle size/shape across the channel. This may include scanning an optical beam across the flow, moving the flow across the beam, or using multiple beams, the transmission/reflection of which are then referenced against one another, either optically (for example, by interference, or by using an optical switch), electronically (for example, by using a differential detector pair), or digitally. In embodiments, an electronic processing system may calculate, based on detection of transmission/reflection of the different sub-flows one or more physical and/or biochemical characteristics of at least one target media constituent.

Figure 6:
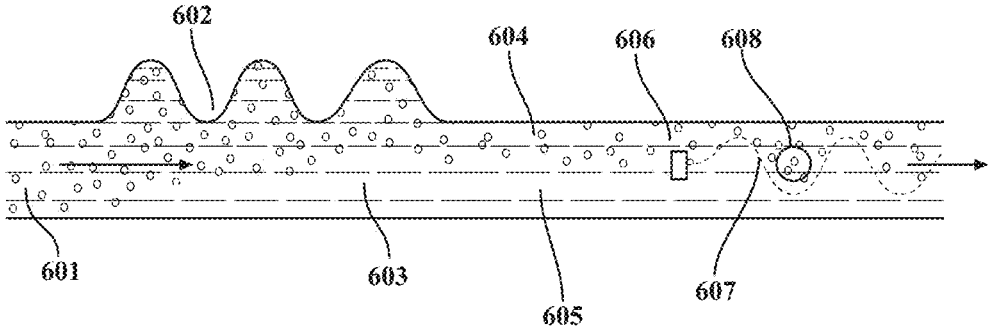
FIG. 6 depicts a flow separating embodiment of the present disclosure.

FIG. 6 depicts another embodiment of the present methods and systems of graded bioprocess constituent measurement disclosed herein. In this embodiment a bioprocess fluids 601 enters and is first separated by a separation section, depicted schematically only here by 602. This section may employ inertial fluidic, or a series of designed obstructions (such as those used in DLD designs) to separate particles of certain sizes from the rest of the flow, as is depicted by 603. In this case, a single "particle" type is pushed to one side of the flow, as shown by 604, leaving the other part of the flow 605 of this particle—establishing a "reference" fluid that may be used to eliminate the common background signal. In this example, an obstruction 606 in the channel downstream of "sorting" is used to generate vortices (represented by the dashed line 607), causing alternating particle-laden and particle-poor fluid to pass an optical interrogation region 608. In this manner, light transmitted through this region alternates between effects of the media and particles, and then only the underlying media. For example, the media may be growth media from a bioreactor, and the particles may be cells from the bioreactor. In another example, these particles may be protein aggregates. In another example, these particles may be extracellular vesicles. In one example, the optical measurement may be transmitted light at one or more wavelengths. In another example, the optical measurement may be scattered light at one or more wavelengths. In another example, the optical measurement may be transmitted light in one or more polarizations. Finally, the liquid exits to a waste stream, or is returned to the bioreactor in the case of a closed-system monitoring application.

Figure 7:
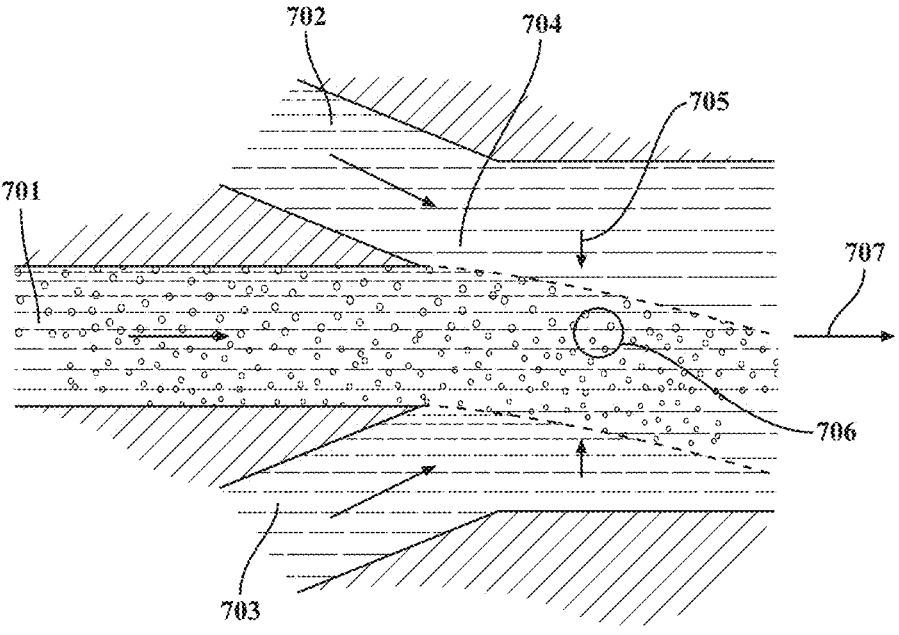
FIG. 7 depicts a sorting embodiment of the present disclosure.

FIG. 7 depicts another embodiment of the methods and systems of graded bioprocess constituent measurement disclosed herein. A liquid that has passed through a subsystem for size-based (and/or shape- and mechanical property-based) sorting of particles/droplets/vesicles/etc. contained in the flow 701 enters the measurement stage shown here, and is combined with two other liquid flows 702 and 703. The liquid used in these flows may be, for example, fresh media, such that the portion of the incoming sorted fluid that contains the fewest (smallest) particles, which is essentially the active media with particles removed, may be measured against fresh media. The three flows 701, 702, and 703 merge at a junction 704 designed to result in a laminar downstream flow 707. The two flows 702 and 703 are modulated such that they shift the central stream from the bioprocess laterally in the combined channel, as indicated by 705. This causes different portions of the size-sorted flow from the bioprocess to be presented to the optical interrogation region, indicated by the circle 706. In this manner, by modulating the pressures/flows of the incoming liquids 702, 703, different portions of the sorted flow 701 are presented, in sequence, to the optical system. This may be done at a relatively high frequency to overcome 1/s noise sources. This allows high-sensitivity measurements of particles of various sizes in the bioprocess media against the substantially empty active media, and of the active media against the fresh media.

FIG. 8 depicts an embodiment of methods and systems of self-modulation. A microfluidic channel structure 801 includes a junction 802 for the purpose of combining two liquids into a single flow. In this case they are combined in laminar flow such that the boundary impinges directly upon an obstruction 803. Downstream from the obstruction, an optical interrogation region 804 is positioned, so as to allow measurements of absorption, scattering/diffraction, fluorescence, or other interactions of the supplied electromagnetic radiation with the fluid flow downstream of the obstruction.

FIG. 9 shows an embodiment of self-modulation in a low-velocity, low-Reynolds number mode. The two liquids (e.g., analyte and reference) 901 flow together in a laminar manner. They arrive at the obstruction, and in this laminar flow regime, recombine smoothly after the obstruction as indicated by 902. They subsequently flow through the optical interrogation region 903 in laminar fashion. The optical interrogation region may be positioned at the center of the flow, or to one side, or there may be multiple optical interrogation regions (for example one in the reference, and one in the analyte liquid). Depending on the flow speed, the optical interrogation regions may detect diffusion between the liquids, including chemical reactions resulting from that diffusion.

Figure 10:
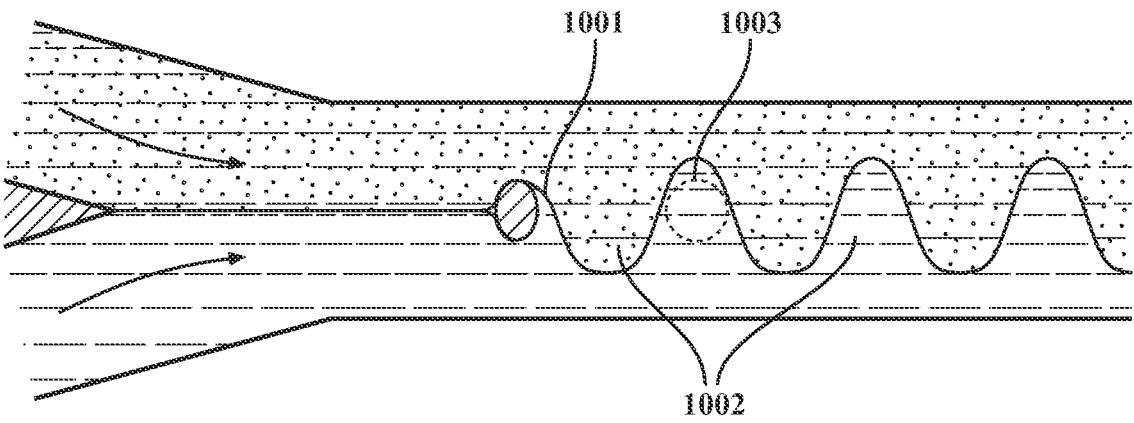
FIG. 10 depicts an exemplary medium-velocity, medium-Reynolds number embodiment.

FIG. 10 depicts an embodiment of self-modulation in a medium-velocity, medium Reynolds number mode. In this mode, the fluid boundary 1001 after encountering the obstruction sets up an oscillating flow known at the "von Karman Street" with vortices moving in alternate directions substantially perpendicular to the main flow (vortex details omitted from drawing for the purpose of simplicity). As a result, a series of alternating incursions of reference and analyte liquid 1002 occur downstream. A properly-positioned optical interrogation region 1003 therefore successively samples primarily reference liquid and then primarily analyte liquid in a predictable temporal pattern. This temporal pattern can be predicted based on fluids viscosities and pressure, be measured to deduce viscosities, or be measured to facilitate adjusting pressure in a feedback control loop, and to facilitate adjusting pressure to achieve optimal self-modulation of the liquid flow past the optical interrogation region.

Figure 11:
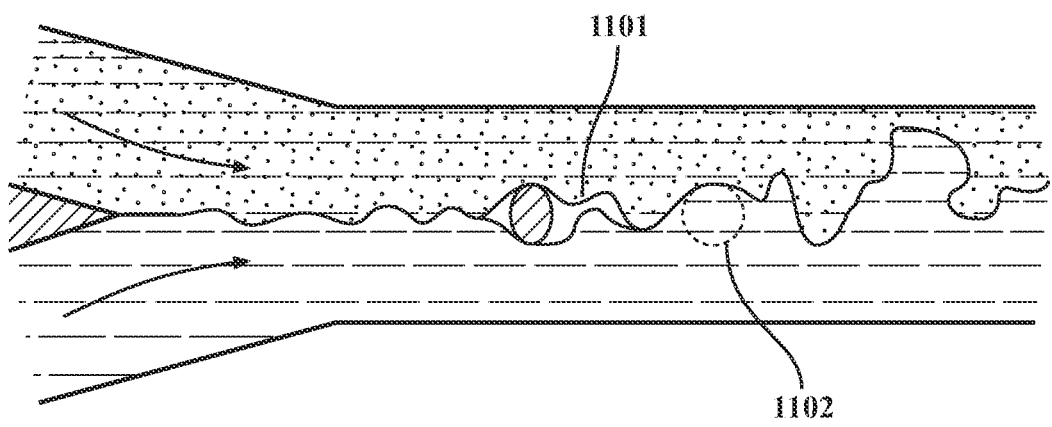
FIG. 11 depicts an exemplary high-velocity, high-Reynolds number embodiment.

FIG. 11 shows an embodiment of self-modulation in a high-velocity, high Reynolds number mode. In this mode, the reference and analyte liquids rapidly devolve into highly turbulent flow 1101 after the obstruction, and the optical interrogation region 1102 samples a mixed liquid region. The level of mixing depends on the position of the optical interrogation from the obstruction. Thus the interrogation region may be moved relative to the obstruction to measure liquids at various stages of interaction, for example to measure a chemical reaction that initiates when the liquids interact.

FIG. 12 shows an embodiment with two optical interrogation regions 1201 and 1202. The regions are positions along the main flow axis such as to simultaneously sample the analyte and reference liquids at certain time points when the self-modulating vortex street is active at medium Reynolds numbers, thus allowing a "difference" to be measured. At low flow rate/Reynolds numbers, the optical regions may both sample the interface between the reference and analyte liquids, thus establishing a baseline signal for the purpose to calibrating the system.

FIG. 13 shows another embodiment with two optical interrogation regions 1301 and 1302. In this embodiment, the regions sample substantially entirely the reference liquid and analyte liquid, respectively, at low flow rates, and then as the flow transitions to a vortex street, sample analyte and reference liquid in alternating fashion, such that at periodic time points one region samples substantially entirely the analyte liquid while the other samples substantially the reference liquid, thus enabling measuring a difference between the analyte and reference liquid.

In embodiments, a difference measurement when two or more optical interrogation regions are used may be performed in a number of manners:

a. Two or more detectors may be used to receive the radiation passing through the two or more interrogation regions, respectively, and electronic signals produced by these detectors may be differenced, either by analog electronic means, or by computer means after conversion from analog to digital signals; in this configuration, a single radiation source may be used and split into beams that pass through the various interrogation regions: in this case variations in the radiation source output are cancelled in the difference measurement.

b. A single detector may be used to receive radiation passing through the two or more interrogation regions, with the optical path being switched such that the detector samples one region at a time; for example, an optical switch or mirror may be used to choose the optical path. Similarly, the radiation source may be deflected towards these interrogation regions successively. Finally, both the path from the radiation source to the regions and from the regions to the detector may be steered.

c. A single detector may be used, and the light passing through the interrogation regions is recombined in a manner as to create an optical difference measurement, such as an interferometric recombination, where two optical branches are split from the light source, used to interrogate the optical regions within the liquid, and then are recombined via another beam combiner, with one at least one branch having an adjustable delay.

In some embodiments, a microfluidic channel with one surface that is reflective at the interrogating wavelength may be used. In this case the radiation from the light source enters from a direction opposite of the reflective surface of the microfluidic channel, passes through the liquid(s), is reflected, and then passes through the liquid(s) again as it exits back towards the direction it entered. Such a configuration can significantly simplify the instrument design, particularly when disposable microfluidic chambers are used.

Figure 14:
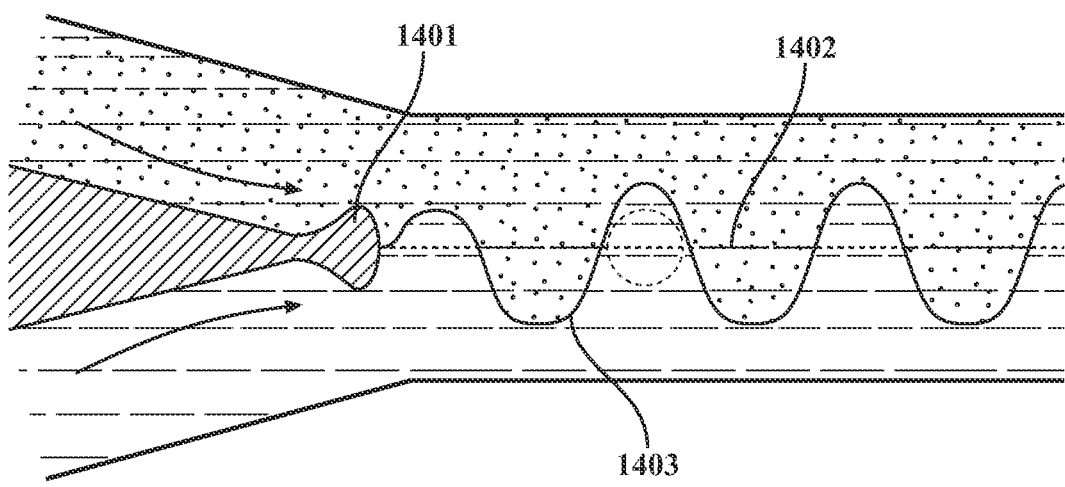
FIG. 14 depicts an exemplary embodiment with a vortex-creating obstruction.

FIG. 14 shows an embodiment of self-modulation where a vortex-creating obstruction 1401 is integrated into the fluid junction where reference and analyte liquid flows are merged. The separated flow at low flow rate is shown with the dashed line 1402; the periodic vortices formed at medium flow are shown as a solid line 1403.

Figure 15:
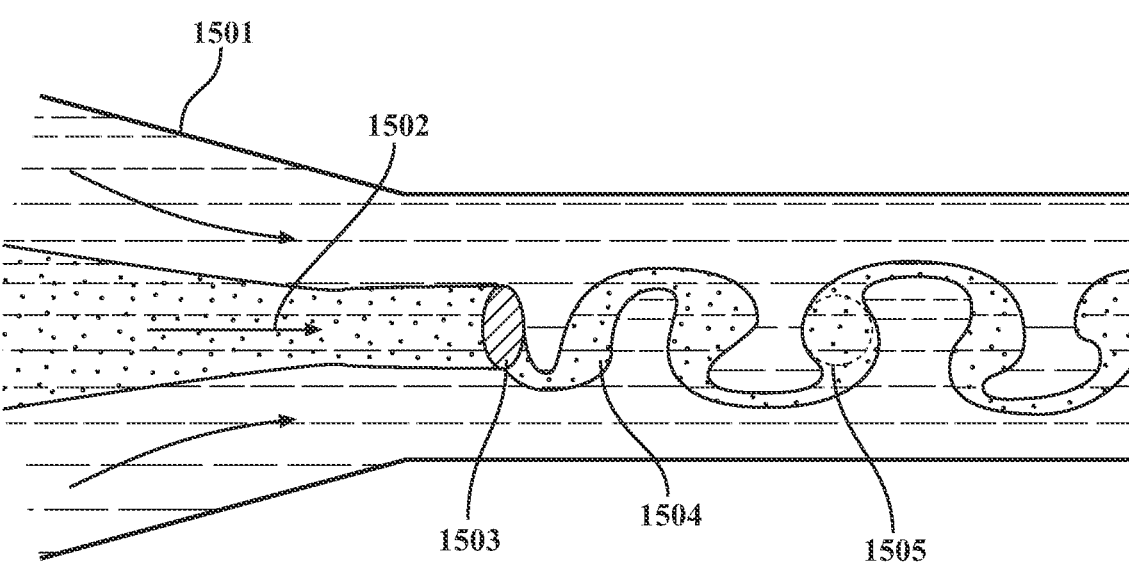
FIG. 15 depicts a three-fluid exemplary embodiment.

FIG. 15 shows another embodiment of self-modulation, where three fluid flows are combined into a laminar flow at a junction 1501 (as is common in cytometry applications);

with a first fluid 1502 flowing in the center. The outer fluids on either side of the first fluid may be identical or different compositions. For example, the first fluid 1502 may be fluid where the analyte has been treated (e.g., by temperature or chemical exposure), while the outer fluids may carry the same analyte but untreated. In this example, the system can measure a differential between treated and untreated analyte. An obstruction 1503 in the microfluidic channel downstream of the junction 1501 causes a vortices 1504 to shed, which in this configuration produces "packets" of the central fluid to process down the center of the downstream channel, alternating with pockets of outer fluid from either side of the central flow. As the pattern of vortices 1504 propagate down the fluid chamber, interrogation region 1505 can be presented with the central fluid, an upper outer fluid, or a lower outer fluid. This configuration may in effect allow 3 liquids to be interrogated with a single optical interrogation region 1505.

Figure 16:
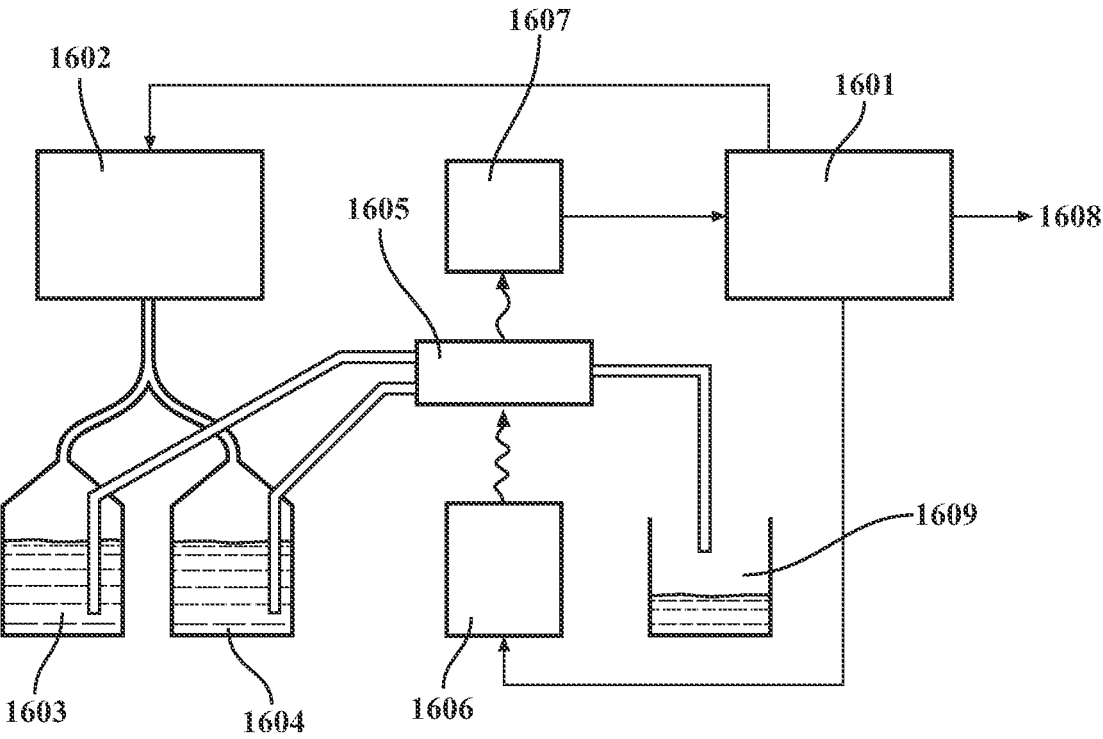
FIG. 16 depicts a system-level block diagram of an exemplary embodiment.

FIG. 16 shows an overall example system diagram of methods and systems of self-modulation. A computing system/controller 1601 commands a pressure generator/regulator 1602, which provides pressure to two liquid source containers 1603 and 1604. This pushes the liquids into the microfluidic flow chamber 1605 where, depending on the pressure applied, the liquids flow in a laminar flow, a vortex-shedding flow, or a fully-turbulent flow as described above. After passing through the flow chamber, the liquid is routed to a waste container 1609. At least one optical source 1606 provides light into the interrogation region(s) in the microfluidic channel, and the transmitted light is measured by at least one detector 1607. The detector signal(s) are provided back to the computing/control system. The control system may measure the signal frequency to estimate the flow condition within the channel; for example, it may measure the sharpness and frequency of the variations in transmission at one or more wavelengths, and from this, determine whether the vortices are optimal for measurement; by continuously measuring this signal and commanding changes to the pressure controller, closed-loop control of the vortex flow is achieved. This control of the flow state may be done using wavelengths other than the wavelength to be used for measuring the analyte(s); for example, a visible-light source and detector (or camera) may be used, and a dye may be added to one or more of the source liquids in order to control the flow, outside of the measurement wavelength band, where the liquids may be virtually identical in some cases. As a desired vortex condition has been achieved, the computing system commands the light source(s) to produce light at the appropriate wavelengths and conditions for measuring the analyte(s), reads the detector output(s), and extracts the signal corresponding to the differences in liquid absorption and/or scattering. The light source and/or detector may be controlled by the control system to (a) illuminate the channel at different wavelengths, or to detect at different wavelengths; (b) illuminate the channel at different locations, or to receive light from different locations; (c) illuminate the channel with different angles, or to receive light at different angles, for example when illuminating/receiving at a diversity of angles in order to measure angular scattering from particles in the liquids; (d) illuminate or receive light at different polarizations; and combinations thereof. At each condition the signal from the modulated flow provides a differential signal at a frequency that can be isolated. The composite of these signals, over the range of conditions, is compiled and provided as an output 1608. Optionally, the computing system may make further calculations specific to the application, for example it may provide immediate measurements of nutrients in fresh vs spent media.

Figure 17:
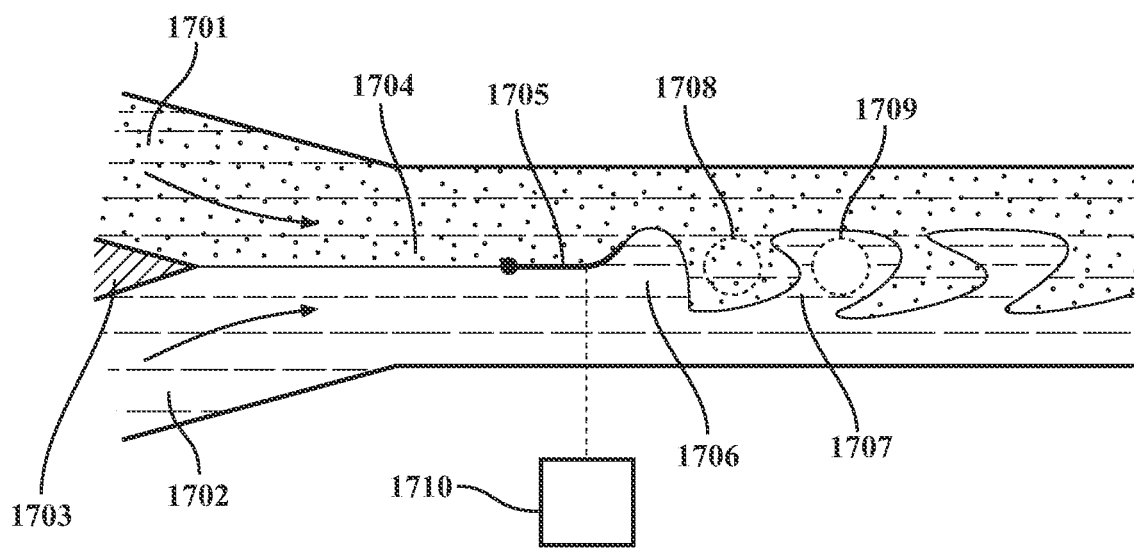
FIG. 17 depicts a flexible membrane exemplary embodiment.

FIG. 17 depicts an embodiment of self-modulation utilizing a flexible membrane to initiate vortex flow at low flow rates (low Reynolds numbers). A first channel 1701 carries a first fluid, and a second channel 1702 carries a second fluid to a laminar flow junction point 1703, where the two fluids join into a parallel laminar flow 1704. A flexible membrane 1705 anchored at the upstream point denoted by the circular section is disposed within the channel at the centerline. As the fluids are pushed past this element at over a threshold velocity, it oscillates at a rate that is at least flow velocity dependent and oscillates over a distance from a midline of oscillation that is at least partially dependent on relative flow velocities, thereby creating downstream vortices 1706. This creates a predictable series of alternating pockets of fluid 1707 passing through a given point downstream and a predictable frequency. An optical measurement point 1708 is then established. At this point, a beam passes through the channel perpendicular to the diagram, and interacts with each fluid successively, at the frequency given by the vortex shedding. The interactions of the radiation with the fluid may include but are not limited to: absorption, scattering, phase shift due to refractive index, Raman scattering, fluorescent excitation. All of these interactions may be wavelength-dependent, and polarization-dependent.

In some embodiments, additional measurement points (1709) may be used. These may be positioned to be sampling a second fluid while the first measurement point 1708 measures a first fluid. In this manner, a momentary differential measurement may be made—in addition to the differential provided by the modulation itself. This may provide additional measurement sensitivity. The light used to sample these points will preferably originate from the identical source, and be split in order to sample these two or more measurement points. In this manner, variations in the source intensity, wavelength, polarization or other characteristics may be cancelled in the measurement. After passing through the measurement points, the light may be directed to independent detectors for detection and processing; in other embodiments it may be directed to detectors that are coupled electronically to provide a differential signal (for example, many pyroelectric detectors are available in differential pairs for this purpose); in other embodiments, the light from the two measurement zones may be recombined optically. In such an arrangement, an interferometric setup may be used to measure very small differences in optical path length through the two fluids (i.e. wavelength-dependent refractive index); in a similar configuration, light split and then recombined by polarization may be used to achieve this measurement.

An additional element shown in this example embodiment is a sensor 1710 which detects the oscillation of the flapping membrane 1705. This sensor provides an independent signal by which the measurement of vortices (and therefore fluids) in the measurement zone 1708 can be synchronized and processed. It may also be used to regulate the flow (or pressure) in the system in order to achieve the desired vortex frequency. This sensor may be using an optical reflection, or an electrical measurement in the channel. It may be done in the plane of the diagram as shown here, or by the use of measurement beams orthogonal to the plane of the paper, much like the measurement beams for the fluids. In some cases, a camera with sufficient frame rate, together with appropriate illumination, objective, and image processing may be used to detect the oscillation of the membrane. It is important to note that the vast majority of cases the fluids will appear identical (without a boundary between them) to a conventional imaging system such as this—but the flexible membrane approach, as opposed to the fixed flow obstructions such as cylinders or rectangular columns, allows direct measurement of the vortex shedding frequency and amplitude using low-cost, visible-light or NIR sensors. The system can then be engineered calibrated with the use of fluids having the same properties as the target fluids, but containing dye visible to a visible-light camera. The correspondence between membrane behavior and downstream vortex formation, boundaries, and mixing may then be established, and used in the control of the instrument.

Figure 18:
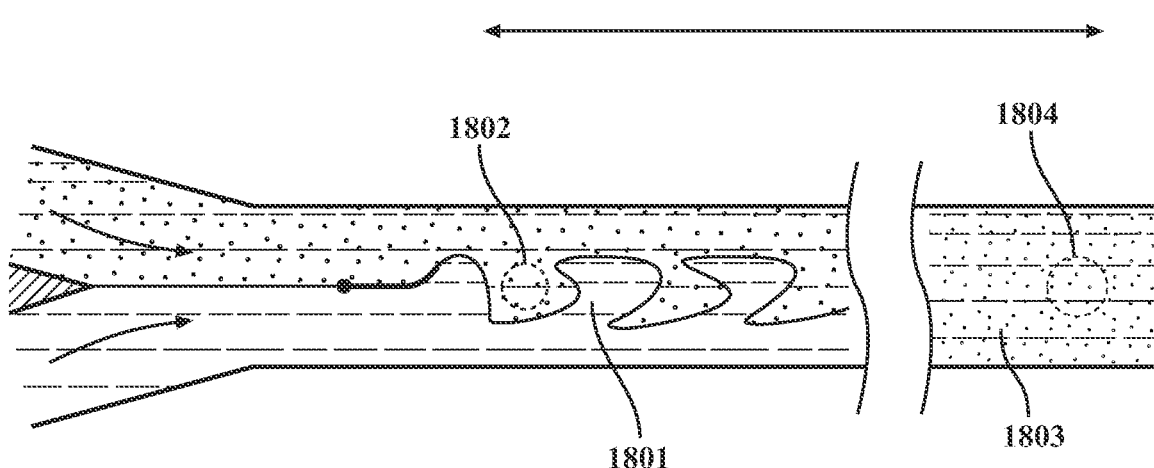
FIG. 18 depicts an embodiment with a flexibly positioned measurement zone.

FIG. 18 depicts an embodiment where a measurement zone can be positioned flexibly along the channel. For example in one region 1801 where the vortices are cleanly separated, the measurement zone position 1802 measures the two fluids successively at the frequency of the vortex shedding. The measurement position may then be moved (most likely accomplished by moving the microfluidic channel) such that the optical measurement zone (now indicated by 1804) measures a region 1803 where the fluids are well-mixed. This may be done with the same flow conditions, or at higher flow rate to achieve more complete mixing. This type of system may be used where there is fluid interaction (such as chemical interaction or biochemical interaction), and it is desirable to measure the individual fluids pre-mixing, and then the post-interaction result. Note in-operation repositioning of the optical measurement zone(s) relative to the channel and obstruction serves a number of purposes in self-modulation, including optimal positioning of the measurement zone(s) along the channel as well as transversely, in order to achieve maximum contrast between the fluid properties in the measurement. This may be done dynamically, using the signal extracted from the measurement zone(s).

Figure 19:
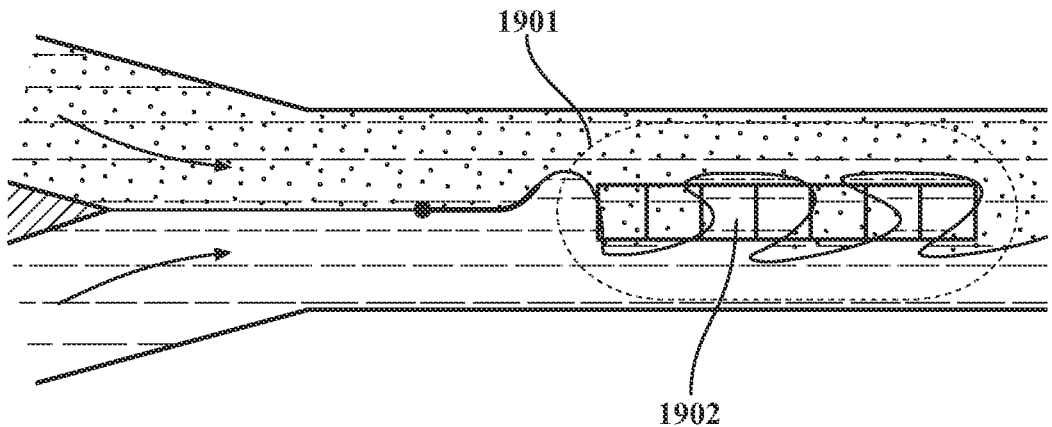
FIG. 19 depicts an embodiment with an array of measurement zones.

FIG. 19 shows an embodiment where an array of measurement zones is used to accomplish the measurement enabled in the methods and systems of self-modulation disclosed herein. In this embodiment, a relatively large zone in the channel is illuminated with a light source, as indicated by 1901. Note this zone may include regions upstream of the obstruction as well, and the obstruction or membrane region itself. The entire zone indicated by 1901 is thereby illuminated, and light is collected after it passes through the fluids by the appropriate optics. Optics are then provided, in this embodiment, to relay the transmitted radiation to an array of detectors—their corresponding areas within the channel are shown by the array 1902. An array such as this, with the appropriate readout electronics, and potentially analog or digital differentials, may be used to both extract a signal with higher SNR, and to dynamically adjust the performance of the fluidic system via pressure or flow controls.

Figure 20:
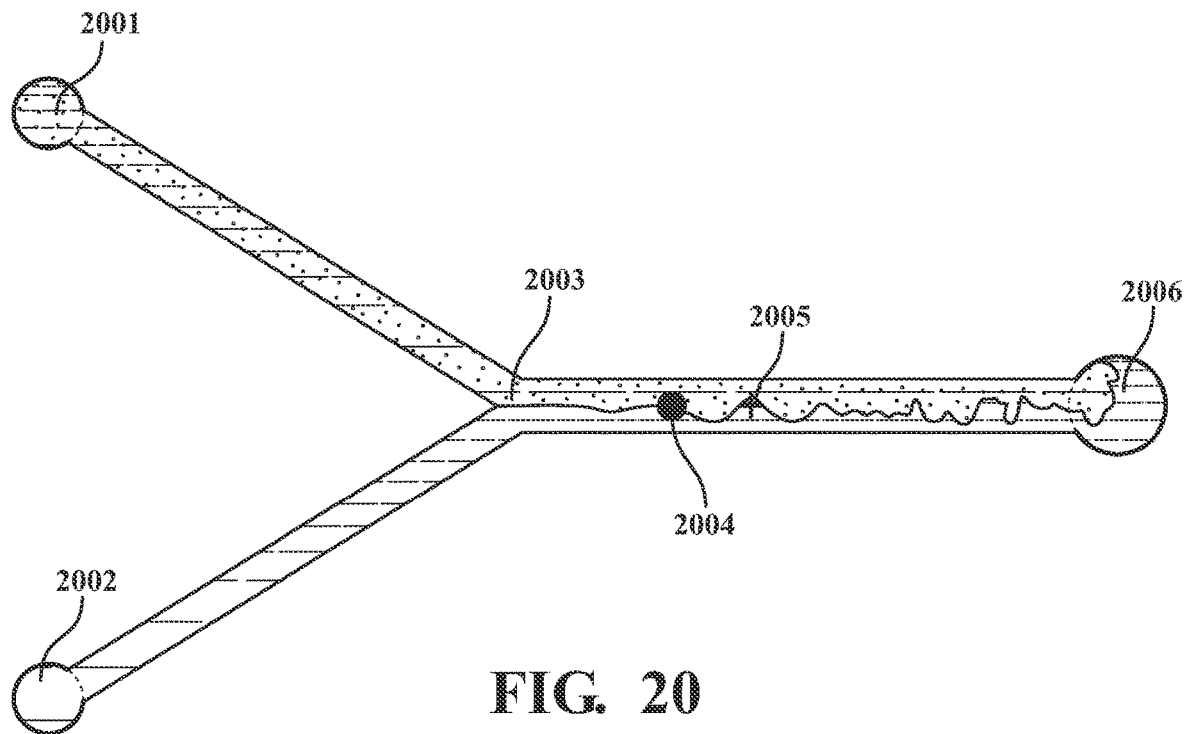
FIG. 20 depicts a first microfluidic channel design embodiment.

FIG. 20 shows a first of two examples of multiple potential microfluidic channel designs for use in self-modulation. FIG. 20 depicts a configuration where two fluid input ports, 2001 and 2002, are used to feed two channels that merge into a laminar flow at junction 2003. An obstruction 2004 sheds vortices downstream, and an optical measurement is made at 2005 of the alternating fluid masses as they pass. A waste port 2006 is used to remove the mixed fluids and typically dispose of them.

Figure 21:
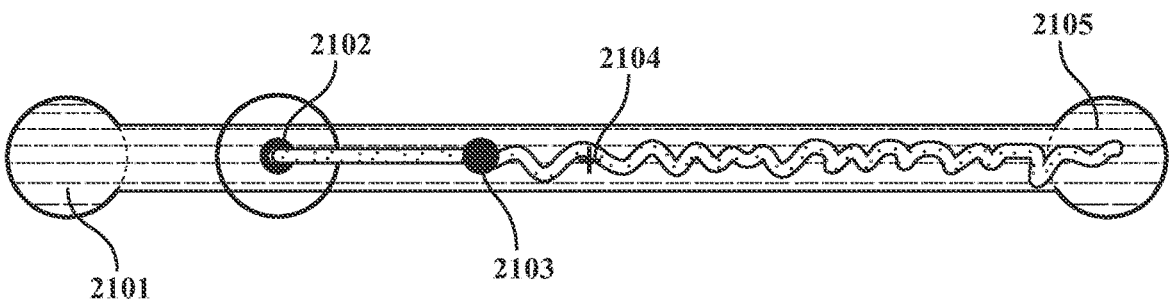
FIG. 21 depicts a second microfluidic channel design embodiment.

FIG. 21 shows a second configuration of two configurations of multiple potential microfluidic channel designs. A first fluid (typically the "reference" fluid) is inserted via a first port 2101. Downstream, a port 2102 at the top of the channel is designed to push in a second fluid, which is entrained in the first fluid in a laminar flow down the center of the channel. An obstruction 2103 then sets up vortices where the first fluid oscillates downstream, across a measurement zone 2104. Finally, a waste port 2105 removes the mixed fluids.

Bioprocess Invention Clauses

In an aspect, a system for monitoring a bioreactor may include a fluid handling system that extracts active media from the bioreactor, at least one filtering stage that splits the media into at least two differently-filtered streams, where one stream of the at least two differently-filtered streams contains at least one target media constituent that is filtered out of other streams of the at least two differently-filtered streams, a fluid combiner that combines the at least two differently-filtered streams into a flow chamber including an optical interrogation region, an optical characteristics measurement subsystem that measures a difference in optical characteristics between the at least two differently-filtered streams within the flow chamber, and an electronic processing system that calculates, based on the optical characteristics measurement one or more of physical characteristics and biochemical characteristics of the at least one target media constituent. In the aspect, the one or more of physical characteristics and biochemical characteristics of the target media constituent facilitates one or more of monitoring and controlling the bioreactor. Further in the aspect, the bioreactor is a continuous perfusion mode bioreactor, and controlling the bioreactor includes controlling addition of fresh media. Also in the aspect, controlling the bioreactor includes controlling withdrawal of one or more of processed media that includes waste products, and target products. Yet further in the aspect, the fluid combiner combines the at least two differently-filtered streams in a substantially parallel laminar flow that maintains a distinct boundary between the at least two differently-filtered streams within the optical interrogation region. Also in the aspect, relative pressures of the two fluids at the distinct boundary moves the distinct boundary orthogonal to a direction of the laminar flow at a media-dependent frequency within the optical interrogation region. Optionally, the flow chamber includes an obstruction in the laminar flow that sets up a vortex modulation prior to the laminar flow entering the optical interrogation region. In the aspect, the optical characteristics measurement subsystem measures optical absorption differences between the at least two differently-filtered streams in one or more wavelength ranges selected from a list of ranges consisting of: Ultra Violet, visible wavelength, Near Infrared, Medium-Wave Infrared, and Long-Wave Infrared. Optionally, the optical characteristics measurement subsystem measures optical absorption at one or more wavelengths in two or more wavelength ranges in the list of wavelength ranges. Yet further in the aspect, the optical characteristics measurement subsystem measures optical absorption for at least two polarizations of light at one or more wavelengths. Also in the aspect, the optical characteristics measurement subsystem measures Raman scattering differences between the at least two differently-filtered streams. In the aspect, the optical characteristics measurement subsystem uses an optical phase differential technique to measure a difference in refractive index between the at least two differently-filtered streams at one or more wavelengths. Yet further in the aspect, the optical characteristics measurement subsystem measures a difference in scattered light at one or more wavelengths between the at least two differently-filtered streams. Optionally, the electronic processing system further determines a source of the scattered light selected from a list of scattered light sources consisting of: aggregates of molecules; aggregates of proteins, viral particles, cells, cell aggregates, extracellular vesicles including exosomes; microcarriers with or without attached cells; and cell debris. The aspect further includes one or more light source selected from a list of light sources consisting of: a wavelength-tunable laser, quantum cascade laser (QCL); and a pulsed laser. In the aspect, the bioreactor is a continuous perfusion mode bioreactor with fresh media continuously added to the bioreactor at a first rate and wherein the one or more of physical characteristics and biochemical characteristics of the target media constituent facilitates adjusting the first rate of fresh media addition. Optionally, the system is adapted to measure cell nutrient concentration and/or cell metabolite concentration.

In the aspect, the bioreactor uses cells to produce one or more target proteins. Optionally, a level of the one or more target proteins is calculated by the electronic processing system.

In the aspect, the bioreactor uses cells to produce viruses, including one or more of viruses for vaccines and viruses for gene therapies. Optionally, the viruses for gene therapies includes one or more of lentiviruses and Adendo-Associated Viruses. Also, a concentration of a target virus is calculated by the electronic processing system.

In the aspect, the bioreactor uses cells to produce one or more of deoxyribonucleic acid (DNA) and ribonucleic acid (RNA). Optionally, a level of one or more of the DNA and the RNA is calculated by the electronic processing system.

In the aspect, the bioreactor produces cells, and a state of the cells is measured by measuring the optical characteristics of the cells. Also, a state of the cells is measured by measuring one or more of cell nutrients and metabolic byproducts.

In the aspect, the bioreactor produces cells where a state of the cells is measured by measuring one or more of extracellular vesicles, extracellular proteins, and other signaling molecules produced by the cells.

The aspect may include one or more of a flow filtration subsystem and a separation subsystem processing the active media to present a pre-filtered version of the active media that includes one or more of: aggregates of molecules, aggregates of proteins, viral particles, cells, cell aggregates, extracellular vesicles including exosomes; microcarriers with or without attached cells; and cell debris.

In another aspect, a system for measuring a media or products of a bioprocess includes a size-separation stage that utilizes a continuous fluidic path with features that separate and sort solid and other immiscible items of the media by one or more of size, shape and mechanical properties, such that the sorted items of the media are arranged orthogonal to the fluidic path in an exit stream of the stage, an optical measurement subsystem that measures at least two of the items of the exit stream to determine a relative measurement of one or more optical properties of the at least two of the items of the exit stream, and an electronic processing system that calculates, based on the relative measurement one or more of physical characteristics and biochemical characteristics of one or more target constituents across the exit stream. In this aspect, the one or more of physical characteristics and biochemical characteristics of the one or more target media constituents facilitates monitoring the bioprocess. Also in this aspect, the optical measurement subsystem measures the at least two of the items of the exit stream in parallel. Yet further within this aspect, the optical measurement subsystem measures the at least two of the items of the exit stream sequentially.

In yet another aspect, a method of monitoring a bioreactor includes extracting active media from the bioreactor, filtering the extracted active media into at least two differently-filtered streams, where one stream of the at least two differently-filtered streams contains at least one target media constituent that is filtered out of other streams of the at least two differently-filtered streams, combining the at least two differently-filtered streams into a flow chamber including an optical interrogation region, measuring a difference in optical characteristics between the at least two differently-filtered streams within the flow chamber, and calculating, with an electronic processing system, based on the optical characteristics measurement one or more of physical characteristics and biochemical characteristics of the at least one target media constituent.

In an aspect of the methods and systems described herein, a microfluid flow system may include a plurality of input ports, each of the plurality of input ports for receiving a liquid; a means for applying pressure to each received liquid; a liquid merge junction that merges the pressurized liquid from each of the plurality of input ports into a merged liquid flow in a microfluid flow channel; an obstruction disposed in the microfluid flow channel that creates a vortex shedding state of the merged liquid as the merged liquid flows past the obstruction; an optical interrogation region disposed at an optical sensing position downstream from the obstruction; an electromagnetic radiation source that delivers, at the optical interrogation region, electromagnetic radiation at one or more wavelengths relevant to an optical characteristic of the merged liquid; a detector that measures a result of the radiation interacting with the merged liquid at the optical interrogation region; and a computing system that receives an output of the detector and calculates a one or more of physical characteristics and biochemical characteristics of the merged liquid based on the output of the detector. In the aspect, the merged liquid comprises a boundary between at least two input liquids and the obstruction is disposed substantially at the boundary. Also in the aspect, the merged liquid includes an analyte liquid and a reference liquid and the obstruction causes the analyte liquid to pass through the optical interrogation region. In the aspect, the obstruction is disposed substantially at a boundary of the analyte liquid and the reference liquid. Yet further in the aspect, the one or more wavelengths relevant to an optical characteristic of the merged liquid is an optical feature of an analyte liquid received at one of the plurality of input ports. Further in the aspect, the vortex shedding state is a laminar flow state that produces a distinct boundary between a first liquid of the merged liquid and a second liquid of the merged liquid. The obstruction in the aspect produces a laminar flow vortex shedding state that facilitates calibration of at least one of the electromagnetic radiation source and the detector. The vortex shedding state in the aspect is dependent on an amount of pressure applied to each received liquid. The vortex shedding state in the aspect is an oscillating vortex flow that causes an alternating sequence of the received liquids of the merged liquid to pass through the optical interrogation region. Further, the computing system in the aspect calculates a differential between the received liquids based on an output of the detector for each of the received liquids that passes through the optical interrogation region. The vortex shedding state in the aspect is a mixed liquid flow in which the received liquids in the merged liquid are mixed for passing through the optical interrogation region. Further, the computing system in the aspect calculates at least one of a presence, concentration, and state of a component in one received liquid responsive to the mixing.

The electromagnetic radiation in the aspect passes through the merged liquid before reaching the detector. The aspect further including a plurality of optical interrogation regions. Further the obstruction facilitates a first received liquid of the merged liquid to flow within a first of the plurality of interrogation regions and a second received liquid of the merged liquid to flow within a second of the plurality of interrogation regions. Also, the obstruction facilitates a first received liquid of the merged liquid to flow within a first of the plurality of interrogation regions and a combination of the received liquids to flow within a second of the plurality of interrogation regions. Yet further, the obstruction is disposed downstream from the merge junction. In the aspect, the obstruction is disposed proximal to the merge junction. The obstruction comprises a flexible membrane that oscil- lates responsive to the pressure applied to each received liquid. Further the oscillating of the flexible membrane is activated when a flow rate of at least one input liquid exceeds an oscillation velocity of the membrane. Also, the optical interrogation region is disposed downstream from the obstruction substantially at a midline of the oscillation. Yet further, the optical interrogation region comprises a plurality of proximal regions disposed along the midline. In the aspect, the obstruction forms the merge junction. Also, the optical interrogation region is disposed to facilitate detecting a result of the radiation interacting distinctly with each of the received liquids based on the vortex shedding state.

In another aspect of the methods and systems described herein, a method of microfluidic self-modulation includes a plurality of method steps including: receiving a plurality of liquids; applying pressure to each of the plurality of received liquids; merging the plurality of received liquids into a merged liquid flow in a microfluid flow channel; creating a vortex shedding state of the merged liquid with an obstruc- tion disposed in the microfluid flow channel; subjecting the merged liquid to electromagnetic radiation at one or more wavelengths relevant to an optical feature of interest in the merged liquid at an optical interrogation region of the channel disposed downstream from the obstruction; detect- ing a result of the radiation interacting with the merged liquid at the optical interrogation region; and calculating with a computing system a property of interest of the merged liquid based on an output of the detecting. In this aspect, the property of interest is a property of a target constituent of one of the plurality of liquids. Also, the one of the plurality of liquids is an analyte liquid. In this aspect, the optical interrogation region is disposed to facilitate detecting a result of the radiation interacting distinctly with each of the plurality of liquids based on the vortex shedding state. The merged liquid comprises a boundary between at least two of the plurality of liquids and the obstruction is disposed substantially at the boundary. The merged liquid includes an analyte liquid and a reference liquid and the obstruction causes the analyte liquid to pass through the optical inter- rogation region. The obstruction is disposed substantially at a boundary of the analyte liquid and the reference liquid. Further, the one or more wavelengths relevant to an optical feature of interest in the merged liquid is an optical feature of an analyte liquid of the plurality of liquids. In the aspect, the vortex shedding state is a laminar flow state that pro- duces a clean boundary between a first liquid of the merged liquid and a second liquid of the merged liquid. Also, the obstruction produces a laminar flow vortex shedding state that facilitates calibration of one or more of the electromag- netic radiation and the detecting. Yet further, the vortex shedding state is dependent on an amount of pressure applied to each received liquid. The vortex shedding state is an oscillating vortex flow that causes an alternating sequence of the received liquids of the merged liquid to pass through the optical interrogation region. In the aspect, the computing system calculates a differential between the received liquids based on an output of the detecting for each of the received liquids that passes through the optical interrogation region. The vortex shedding state is a mixed liquid flow in which the received liquids in the merged liquid are mixed for passing through the optical interrogation region. The aspect further includes calculating at least one of a presence, concentration, and state of a component in one received liquid responsive to the mixing. In the aspect, electromagnetic radiation passes through the merged liquid before being detected. The aspect further including dispos- ing a plurality of optical interrogation regions. Also, the obstruction facilitates a first received liquid of the merged liquid to flow within a first of the plurality of optical interrogation regions and a second received liquid of the merged liquid to flow within a second of the plurality of optical interrogation regions. In the aspect, the obstruction facilitates a first received liquid of the merged liquid to flow within a first of the plurality of optical interrogation regions and a mixture of the received liquids to flow within a second of the plurality of optical interrogation regions. The obstruc- tion is disposed downstream from a merge junction of the plurality of received liquids. In the aspect, the obstruction is disposed proximal to the merge junction. The obstruction comprises a flexible membrane that oscillates responsive to the pressure applied to each received liquid. In the aspect, the oscillating of the flexible membrane is activated when a flow rate of at least one received liquid exceeds an oscilla- tion velocity of the membrane. In the aspect, the optical interrogation region is disposed downstream from the obstruction substantially at a midline of the oscillation. The optical interrogation region comprises a plurality of optical interrogation regions that are proximally disposed along the midline. The obstruction is disposed at a formation point within the microfluid flow channel of the merged liquid. And the optical interrogation region is disposed to facilitate detecting a result of the radiation interacting distinctly with each of the received liquids based on the vortex shedding state.

While the disclosure has been disclosed in connection with the preferred embodiments shown and described in detail, various modifications and improvements thereon will become readily apparent to those skilled in the art. Accord- ingly, the spirit and scope of the present disclosure is not to be limited by the foregoing examples, but is to be under- stood in the broadest sense allowable by law.

What is claimed is:

1. A microfluid flow system comprising:
a plurality of input ports, each of the plurality of input ports for receiving a liquid;
a means for applying pressure to each received liquid;
a liquid merge junction that merges the pressurized liquid from each of the plurality of input ports into a merged liquid flow in a microfluid flow channel;
an obstruction disposed in the microfluid flow channel that creates a vortex shedding state of the merged liquid as the merged liquid flows past the obstruction;
an optical interrogation region disposed at an optical sensing position downstream from the obstruction;
an electromagnetic radiation source that delivers, at the optical interrogation region, electromagnetic radiation at one or more wavelengths relevant to an optical characteristic of the merged liquid;

a detector that measures a result of the radiation interacting with the merged liquid at the optical interrogation region; and a computing system that receives an output of the detector and calculates a one or more of physical characteristics or biochemical characteristics of the merged liquid based on the output of the detector.

2. The system of claim 1, wherein the merged liquid comprises a boundary between at least two of the received liquids, and wherein the obstruction is disposed substantially at the boundary.

3. The system of claim 1, wherein the obstruction causes a laminar flow state that produces a distinct boundary between a first liquid of the merged liquid and a second liquid of the merged liquid.

4. The system of claim 1, wherein the vortex shedding state of the merged liquid is an oscillating vortex flow that causes an alternating sequence of a portion of the received liquids to pass through the optical interrogation region.

5. The system of claim 4, wherein the computing system calculates a differential between the received liquids based on an output of the detector one or more liquids of the portion of the received liquids that passes through the optical interrogation region.

6. The system of claim 1, wherein the vortex shedding state is a mixed liquid flow in which the received liquids in the merged liquid are mixed for passing through the optical interrogation region.

7. The system of claim 6, wherein the computing system calculates at least one of a presence, concentration, and state of a component in one received liquid responsive to the mixing.

8. The system of claim 1, wherein the obstruction comprises a flexible membrane that oscillates responsive to the pressure applied to each received liquid.

9. The system of claim 8, wherein the optical interrogation region comprises a plurality of proximal regions disposed along a midline of the oscillation.

10. The system of claim 1, wherein the obstruction forms the liquid merge junction.

11. A microfluid flow system comprising:

a liquid merge junction that merges a plurality of pressurized liquids into a merged liquid flow of a microfluid flow channel that is configured to create a vortex shedding state of the merged liquid flow;

an electromagnetic radiation source that delivers electromagnetic radiation to the merged liquid flow in the vortex shedding state at one or more wavelengths relevant to an optical characteristic of the merged liquid flow; and a computing system that monitors the delivery of the electromagnetic radiation to the merged liquid flow and calculates one or more of physical characteristics or biochemical characteristics of the merged liquid flow based on the monitoring.

12. The system of claim 11, wherein the vortex shedding state is a laminar flow state that produces a clean boundary between a first liquid of the merged liquid flow and a second liquid of the merged liquid flow.

13. The system of claim 11, further including an optical interrogation region that is disposed to facilitate detecting a result of the electromagnetic radiation interacting distinctly with one or more liquids in the merged liquid flow based on the vortex shedding state.

14. The system of claim 13, wherein the microfluid flow channel is configured to create an oscillating vortex flow that causes an alternating sequence of a portion of the plurality of pressurized liquids to pass through the optical interrogation region.

15. The system of claim 11, wherein the microfluid flow channel is configured with an obstruction that creates the vortex shedding state.

16. The system of claim 15, wherein the obstruction is disposed proximal to the liquid merge junction.

*    *    *    *    *